(12) United States Patent
Klee et al.

(10) Patent No.: US 6,998,111 B2
(45) Date of Patent: Feb. 14, 2006

(54) STORAGE STABLE POLYMERIZABLE COMPOSITIONS

(75) Inventors: Joachim E. Klee, Radolfzell (DE); Uwe Walz, Constance (DE)

(73) Assignee: Dentaply DeTrey GmbH, Constance (DE)

( * ) Notice: Subject to any disclaimer, the term of this patent is extended or adjusted under 35 U.S.C. 154(b) by 0 days.

(21) Appl. No.: 10/634,506

(22) Filed: Aug. 5, 2003

(65) Prior Publication Data

US 2004/0029995 A1 Feb. 12, 2004

Related U.S. Application Data

(63) Continuation of application No. 09/419,497, filed on Oct. 18, 1999, now abandoned, which is a continuation of application No. 09/064,969, filed on Apr. 23, 1998, now abandoned.

(51) Int. Cl.
*A61K 7/16* (2006.01)

(52) U.S. Cl. .......................................... 424/49; 524/751
(58) Field of Classification Search ................ 424/49; 524/751; 433/226, 228.1
See application file for complete search history.

(56) References Cited

U.S. PATENT DOCUMENTS

| | | | | |
|---|---|---|---|---|
| 4,250,325 A | 2/1981 | Floyd, Jr. et al. | ............. | 560/121 |
| 4,269,960 A | 5/1981 | Gaylord | ....................... | 526/213 |
| 4,482,679 A | 11/1984 | Irving | ...................... | 525/327.3 |
| 4,832,745 A | 5/1989 | Antonucci | ..................... | 106/35 |
| 4,870,191 A | 9/1989 | Wiegand et al. | ............. | 549/214 |
| 4,918,136 A * | 4/1990 | Kawaguchi et al. | ......... | 524/751 |
| 5,166,117 A | 11/1992 | Imai et al. | ................... | 502/169 |
| 5,338,773 A | 8/1994 | Lu et al. | ...................... | 523/116 |
| 5,378,785 A | 1/1995 | Mitra | .......................... | 526/316 |
| 5,501,727 A | 3/1996 | Wang et al. | ................... | 106/35 |
| 5,688,883 A * | 11/1997 | Klee et al. | ................... | 526/141 |
| 5,710,194 A | 1/1998 | Hammesfahr et al. | ....... | 523/116 |
| 5,750,735 A | 5/1998 | Lin et al. | ..................... | 549/475 |

FOREIGN PATENT DOCUMENTS

| | | |
|---|---|---|
| DE | 1 003 448 | 8/1958 |
| EP | 0 115 948 | 10/1986 |
| EP | 0 115 410 | 5/1987 |
| EP | 0 120 559 | 12/1988 |
| EP | 0 277 413 | 4/1992 |
| EP | 0 335 645 | 8/1992 |
| EP | 0 732 098 | 9/1996 |
| JP | 1-168776 | 7/1989 |
| WO | WO 98/43596 | * 10/1998 |

OTHER PUBLICATIONS

Antonucci J. New Initiator Systems for Dental Resins Based on Ascorbic Acid. J Dental Research Sep. 1979, 58(9)1887-1899.*
J. Lal et al., J. Polym. Sci. 24 (1957) 75.
J. M. Antonucci et al., J. Dent. Res. 58 (1979) 1887.
G. Sauvet et al., J. Appl. Polym. Sci.: Part A, Polym. Chem. 32 (1994) 1459, 1470.

* cited by examiner

*Primary Examiner*—Ralph Gitomer
(74) *Attorney, Agent, or Firm*—Daniel W. Sullivan; James B. Bieber; Douglas J. Hura

(57) ABSTRACT

A composition is adapted to be stored for at least 24 hours at between 0° C. to 40° C. and between 0 percent and 100 percent humidity. The composition includes from 0.2 to 5 percent by weight of a peroxide, from 0.2 to 3 percent by weight of a metal containing material, from 0.1 to 3 percent by weight of a protected reducing agent. The protected reducing agent is adapted to form an active reducing agent. Optionally the composition includes from 0 to 1 percent by weight of an amine.

13 Claims, 1 Drawing Sheet

STORAGE STABLE POLYMERIZABLE COMPOSITIONS

This application is a continuing application of 09/419,497 filed Oct. 18, 1999, now abandoned, which is a continuing application of 09/064,969 filed Apr. 23, 1998, now abandoned.

The invention relates to storage stable polymerizable dental compositions. A polymerizable composition of the invention includes a peroxide which decomposes by fifty percent during 10 hours at temperatures higher than 75° C., a protected reducing agent which forms an active reducing form under acidic or basic conditions, a metal salt or an organ-metallic compound and an amine. Compositions of the invention comprising the protected reducing agent are stable under the conditions of increased temperature and humidity.

TECHNICAL BACKGROUND

Thermal polymerization initiators are required for a number of dental materials that polymerize under conditions in which initiation of polymerization by light is inefficient. Frequently, thermal setting dental cements are used for the adherence of ceramic or metallic restorations. Also the application of more opaque materials makes a self-curing thermal polymerization initiator necessary. Advantageous is a thermal polymerization initiator in cases when a polymerization in the depth is required or a larger quantity of material is used, such as for a temporary crown and bridge material. A large number of thermal setting materials comprise peroxide/amine initiators; most of them comprise BPO or modified BPO and amines. Only in individual cases other redox-initiators are used, such as peroxide/metal ions (reduction agents such as ascorbic acid), or metal carbonyl compounds/organic halogenides, or boralkyle compounds/oxygen, or persulfate/mercaptane, or sulfinate/metal compounds. Dental materials must fulfill some special conditions for patient comfort, convenience and safety. Polymerization of dental materials must occur at relatively low temperatures (about 37° C.) in bulk with high rates of polymerization and high degree of polymerization (resulting in at most a minute percentage of residual monomer). They should have a long shelf-life for a period of at least 18 month, which means that they should be thermostable at ambient temperature and do not decompose under moisture conditions. Furthermore, the oxygen inhibited layer should be minimized.

The commonly used dibenzoyl peroxide/amine initiator systems have the advantage of a rapid polymerization of monomers and a relatively thin oxygen inhibited layer. Furthermore, such initiators resist moisture. Disadvantages of commonly used dibenzoyl peroxide/amine initiator systems are the thermal-self decomposition of dibenzoyl peroxide (BPO) and the discoloration of the aromatic amines used. Due to the thermal decomposition of BPO the useful life-time (storage period after which the composition remains useful) of a prior art dental/medical composition is very short.

It is well known that other peroxides than dibenzoyl peroxide do not react with amines (J. Lal et al., J. Polym. Sci. 24 (1957) 75). Furthermore, a number of other initiator systems consisting of BPO or peroxides with a higher thermostability than BPO and metal compounds are used. But these systems are more influenced by oxygen therefor they are forming larger oxygen inhibited layers than peroxide/amine systems. The influence of oxygen is reduced if reductants such as glucose or ascorbic acid are used as coinitiators. Recently, a polymerization initiator was described comprising a peroxide, a metal salt and ascorbic acid (J. M. Antonucci et al., J. Dent. Res. 58 (1979) 1887; U.S. Pat. No. 404,402). Using this initiator dental materials were obtained having high mechanical properties. Disadvantageous is the self-oxidation of ascorbic acid due to moisture. Consequently, the initiator system losses a part of the coinitiator. Due to the oxidation of ascorboc acid the system discolorates intensively yellow. Further experiments were done using barbituric acid or thiobarbituric acid (U.S. Pat. No. 5,166,117). Polymerization initiators comprising BPO, a sulfinate and an amine were used by Kurraray (EP 0115410, 0115948, 0120559, 0277413). As sulfinate were used benzolsulfinate and as amine N,N-di-(hydroxyethyl)-p-toluidine. Polymerization initiators comprising of sulfinate/metal ions are suitable for production of artificial teeth, inlays and onlays. Furthermore the are usable in dental composites comprising MMA/PMMA. Disadvantageous is the bulk polymerization of methacrylates with this initiator due to the formation of an unpolymerized layer between the tooth and the polymer, which avoid the adhesion to teeth tissues. Bredereck had used as polymerization initiators inorganic salts of sulfinic acid, hydrohalogenides and some times peroxide (DE 1 003 448). Recently, a polymerization initiator was described consisting of cumen hydroperoxide, saccharin, copper or iron saccharinate an N,N-di(hydroxyethyl)-p-toluidine without evidence of the suitablity for technical applications (J. Appl. Polym. Sci., Part A, Polym. Chem. 32 (1994) 1459, 1470). In both publications it is shown that the effectivity of the initiator strongly depends on the participants of the initiator system. Only an exchange of copper saccharinate against iron saccharinate lead to a degree of the constant of polymerization of about 2 orders by magnitude. The concentration of the compounds of the initiator system are to low for dental/medical application.

One of the main desires of the prior art has been to find an efficient thermal polymerization initiator that has a long term thermal stability and a long term moisture stability. provides an efficient thermal polymerization initiator that has a long term thermal stability and a long term moisture stability.

Substituted as used herein refers to a fully or partially a halogen substituted moiety.

Unsubstituted as used herein refers to a moiety in which hydrogen is not substituted for by other atoms.

Alkyl as used herein refers to a paraffinic hydrocarbon group.

Alkylene as used herein refers to a hydrocarbon moiety having at least one double bond between two adjacent carbon atoms.

Cyclo alkenyl as used herein refers to a cyclic alkenyl moiety. For example a moiety having the structural formula

Cyclo alkyl as used herein refers to a cyclic alkyl moiety. For example a moiety having the structural formula Arylalkenyl as used herein refers to a moiety having an aryl group and an olefinic group. For example a moiety having the structural formula

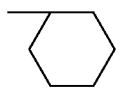

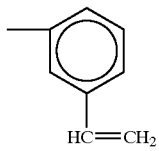

Arylalkyl as used herein refers to a moiety having an aryl group and an olefinic group. For example a moiety having the structural formula

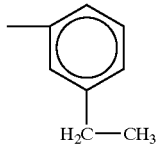

Alkyl aryl as used herein refers to a moiety having an alkyl group and an aryl group. For a moiety having the structural formula

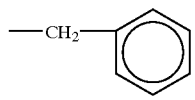

Alkenyl aryl as used herein refers to a moiety having an alkenyl group and an aryl group. For example a moiety having the structural formula

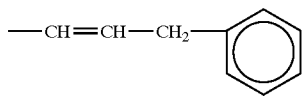

Alkyl aryl alkyl as used herein refers to a moiety having two alkyl groups and an aryl group. For example a moiety having the structural formula

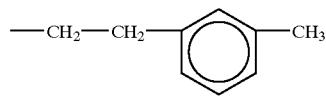

Acylalkyl as used herein refers to a moiety having an acyl group and an alkyl group. For example a moiety having the structural formula

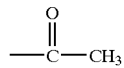

Acyl aryl alky as used herein refers to a moiety having an acyl group, an aryl group and an alkyl group. For example a moiety having the formula

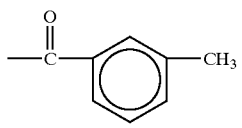

BRIEF DESCRIPTION OF THE INVENTION

The invention provides a thermal polymerization initiating composition, that withstands the temperatures of from 0° C. to 40° C. and humidity of from 0 percent to 100 percent, comprising from 0.2 to 5 percent by weight of a peroxide which decomposes by at most fifty percent by weight of the peroxide within 10 hours at a temperature of at least 75° C., from 0.2 to 3 percent by weight of a metal containing material, from 0.1 to 3 percent by weight of an inactive protected reducing agent that forms the active reducing agent, from 0 to 1 percent by weight of an amine.

DETAILED DESCRIPTION OF THE INVENTION

Figure 1:
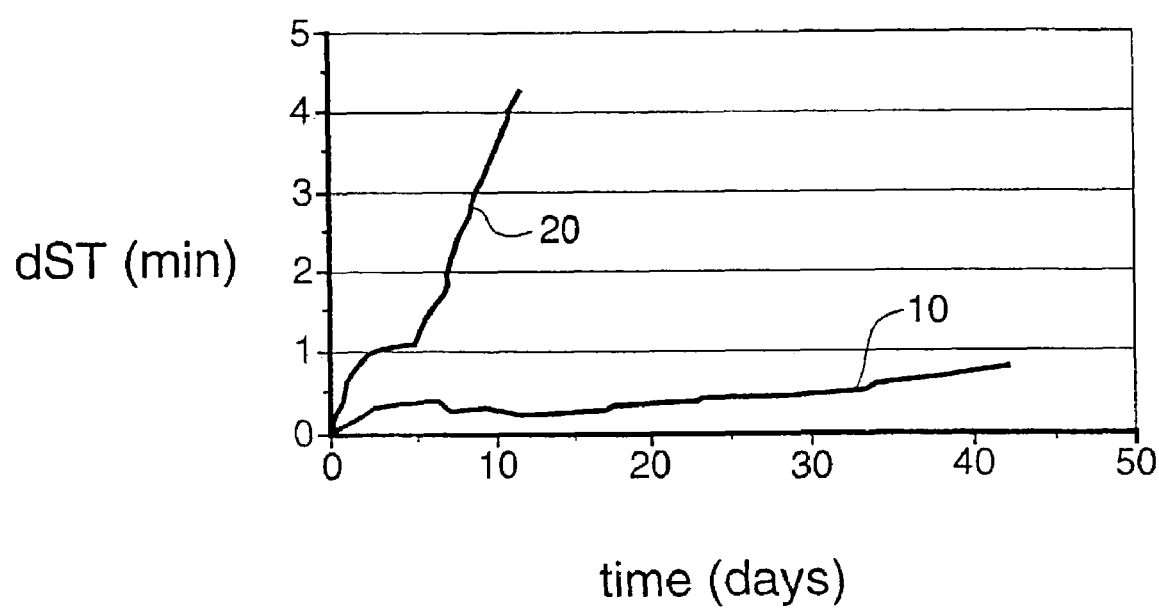
FIG. 1 is a graph of differences in setting time (d ST) verses time for compositions made in accordance with the invention.

The invention provides a polymerizable composition, that withstands the temperatures of from 0° C. to 40° C. and humidity of from 0 percent to 100 percent. The composition includes from 0.2 to 5 percent by weight of a peroxide which decomposes by at most fifty percent by weight within 10 hours at a temperature of at least 75° C., from 0.2 to 3 percent by weight of a metal containing material, from 0.1 to 3 percent by weight of an inactive protected reducing agent that forms the active reducing agent, and from 0 to 1 percent by weight of an amine.

Preferably, protected reducing agent compounds useful in accordance with the invention are characterized by the following structure

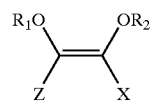

wherein $R_1$ is hydrogen, substituted or unsubstituted alkyl having from 1 to 18 carbon atoms, a substituted or unsubstituted alkenyl having from 2 to 18 carbon atoms, substituted or unsubstituted acylalkyl having from 2 to 18 carbon atoms, substituted or unsubstituted cycloalkyl having from 5 to 18 carbon atoms, substituted or unsubstituted acylcycloalkyl having from 5 to 18 carbon atoms, substituted or unsubstituted arylalkyl having from 5 to 18 carbon atoms or substituted or unsubstituted heteroarylalkyl having from 5 to 18 carbon atoms, substituted or unsubstituted acylarylalkyl having from 5 to 18 carbon atoms or substituted or unsubstituted acylheteroarylalkyl having from 5 to 18 carbon atoms, substituted or unsubstituted alkyl arylalkenyl having from 7 to 30 carbon atoms, substituted or unsubstituted acylalkenyl arylalkyl having from 7 to 30 carbon atoms, or a moiety comprising Si, S or N. Preferably $R_1$ is $Si(R_5)_3$, wherein $R_5$ is substituted or unsubstituted alkyl having from 1 to 18 carbon atoms, substituted or unsubstituted cycloalkyl having from 5 to 18 carbon atoms, substituted or unsubstituted arylalkyl having from 6 to 18 carbon atoms, substituted or unsubstituted alkenyl arylalkyl having from 7 to 30 carbon atoms, $R_2$ is a substituted or unsubstituted alkyl having from 1 to 18 carbon atoms, substituted or unsubstituted acylalkyl having from 2 to 18 carbon atoms, substituted or unsubstituted cycloalkyl having from 5 to 18 carbon atoms, substituted or unsubstituted acylcycloalkyl having from 5 to 18 carbon atoms, substituted or unsubstituted arylalkyl having from 5 to 18 carbon atoms or substituted or unsubstituted heteroarylalkyl having from 5 to 18 carbon atoms, substituted or unsubstituted acylarylalkyl having from 5 to 18 carbon atoms or substituted or unsubstituted acylheteroarylalkyl having from 5 to 18 carbon atoms, substituted or unsubstituted alkyl arylalkyl having from 7 to 30 carbon atoms, substituted or unsubstituted acylalkyl arylalkyl having from 7 to 30 carbon atoms, or a moiety comprising Si, S or N. Preferably $R_2$ is $Si(R_5)_3$ wherein $R_5$ is substituted or unsubstituted alkyl having from 1 to 18 carbon atoms, substituted or unsubstituted cycloalkyl having from 5 to 18 carbon atoms, substituted or unsubstituted arylalkyl having from 6 to 18 carbon atoms, substituted or unsubstituted alkyl arylalkyl having from 7 to 30 carbon atoms, X and Z are substituted or unsubstituted alkyl having from 1 to 18 carbon atoms, substituted or unsubstituted acylalkyl having from 1 to 18 carbon atoms, substituted or unsubstituted cycloalkyl having from 5 to 18 carbon atoms, substituted or unsubstituted acylcycloalkyl having from 5 to 18 carbon atoms, substituted or unsubstituted arylalkyl having from 5 to 18 carbon atoms or substituted or unsubstituted heteroarylalkyl having from 6 to 18 carbon atoms, substituted or unsubstituted acylarylalkyl having from 5 to 18 carbon atoms or substituted or unsubstituted acylheteroarylalkyl having from 6 to 18 carbon atoms, substituted or unsubstituted alkyl arylalkyl having from 7 to 30 carbon atoms, substituted or unsubstituted acylalkyl arylalkyl having from 7 to 30 carbon atoms.

Preferred substituted moieties are fully or partially halogen substituted protected reducing agent compounds include derivatives of ascorbic acid, 2,3-dihydroxy propenal, squaric acid, 1,2-dihydroxy cyclopenten-3,4,5-trion, dihydroxy fumaric acid

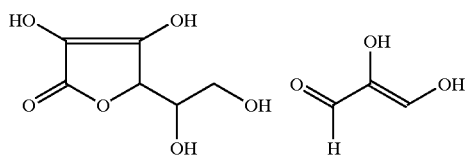

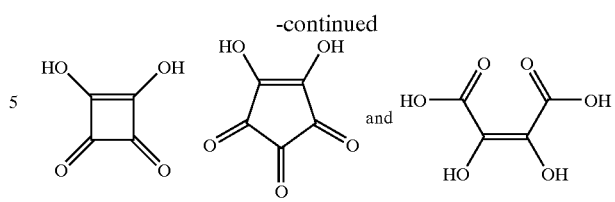

Preferred derivatives of ascorbic acid are characterized by the following structure

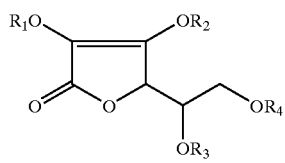

wherein $R_1$ is a hydrogen atom, substituted or unsubstituted alkyl having from 1 to 18 carbon atoms, a substituted or unsubstituted alkenyl having from 2 to 18 carbon atoms, substituted or unsubstituted acylalkyl having from 2 to 18 carbon atoms, substituted or unsubstituted acylalkyl having from 2 to 18 carbon atoms, substituted or unsubstituted cycloalkyl having from 5 to 18 carbon atoms, substituted or unsubstituted acylcycloalkyl having from 5 to 18 carbon atoms, substituted or unsubstituted arylalkyl having from 5 to 18 carbon atoms or substituted or unsubstituted heteroarylalkyl having from 5 to 18 carbon atoms, substituted or unsubstituted acylarylalkyl having from 5 to 18 carbon atoms or substituted or unsubstituted acylheteroarylalkyl having from 5 to 18 carbon atoms, substituted or unsubstituted alkenyl arylalkyl having from 7 to 30 carbon atoms, substituted or unsubstituted acylalkyl arylalkenyl having from 7 to 30 carbon atoms, or $Si(R_5)_3$ wherein R5 is substituted or unsubstituted alkyl having from 1 to 18 carbon atoms, substituted or unsubstituted cycloalkyl having from 5 to 18 carbon atoms, substituted or unsubstituted arylalkyl having from 6 to 18 carbon atoms, substituted or unsubstituted alkenyl arylalkyl having from 7 to 30 carbon atoms and $R_2$, $R_3$ and $R_4$ each independently are substituted or unsubstituted alkyl having from 1 to 18 carbon atoms, substituted or unsubstituted alkenyl having from 2 to 18 carbon atoms, substituted or unsubstituted acylalkyl having from 2 to 18 carbon atoms, substituted or unsubstituted acylalkyl having from 2 to 18 carbon atoms, substituted or unsubstituted cycloalkyl having from 5 to 18 carbon atoms, substituted or unsubstituted acylcycloalkyl having from 5 to 18 carbon atoms, substituted or unsubstituted arylalkyl having from 5 to 18 carbon atoms or substituted or unsubstituted heteroarylalkyl having from 5 to 18 carbon atoms, substituted or unsubstituted acylarylalkyl having from 5 to 18 carbon atoms or substituted or unsubstituted acylheteroarylalkyl having from 5 to 18 carbon atoms, substituted or unsubstituted alkenyl arylalkyl having from 7 to 30 carbon atoms, substituted or unsubstituted acylalkyl arylalkyl having from 7 to 30 carbon atoms, or $Si(R_5)_3$ wherein $R_5$ is substituted or unsubstituted alkyl having from 1 to 18 carbon atoms, substituted or unsubstituted alkenyl having from 2 to 18 carbon atoms, substituted or unsubstituted cycloalkyl having from 5 to 18 carbon atoms, substituted or unsubstituted arylalkyl having from 6 to 18 carbon atoms, substituted or unsubstituted alkyl arylalkyl having from 7 to 30 carbon atoms.

The modified ascorbic acid is modified by acetalisation, silylation, esterification, etherification in this manner, that these protecting groups are removable under acid conditions. For example ascorbic acid is modified using 3,4-Dihydro-2H-pyran, p-nitro-benzoic acid, benzaldehyd, t-butyl alcohol, hexamethyldisilazane (HMDS).

Useful peroxides in this system are those of the type of diacyl peroxides, peresters, perketales, peroxy dicarbonates, dialkyl peroxides, ketone peroxides or alkyl hydroxy peroxides. Preferably were used 2,5-dimethyl-2,5-di(benzolyperoxy)hexane, tert.-butylamyl peroxide, di-(tert.-butyl) peroxide, tert.-butylhydro peroxide, tert.-butylperoxy-(3,5,5-trimethylhexanoate), tert.-butylperoxy-2-ethylhexylcarbonate, tert.-butylhydro peroxide.

Peroxides useful in compositions in accordance with the invention decompose by at least 50 percent by weight within 10 hours at temperatures higher than 72° C. Exemplary peroxides which are useful in compositions in accordance with the invention are shown in Table 1. Dibenzoyl peroxide is not useful in composition of the invention: ($T_{1/2}$ (10 h)=72° C.).

TABLE 1

| Peroxide | $T_{½}$ (10 h) |
|---|---|
| 2,5-Dimethyl-2,5-di(benzoylperoxy)hexane | 100° C. |
| tert.-Butylperoxy-(3,5,5-trimethylhexanoate) | 100° C. |
| tert.-Butylperoxybenzoate | 104 |
| tert.-Butylamyl peroxide | 104° C. |
| Di-(tert.-butyl) peroxide | 125° C. |
| tert.-Butylhydro peroxide | 170° C. |

Amines useful in compositions in accordance with the invention include alkyl aryl amines, dialkyl aryl amines, trialkyl amines or derivatives therefrom. Preferred amines useful in compositions in accordance with the invention are N,N-bis(hydroxyethyl)-p-toluidine, N,N-diethyl-p-benzoic acid ethyl ester, tributylamine.

Metal containing material useful in compositions in accordance with the invention include salts of a metal or an organo-metalic compounds. Organo-metalic compounds may be derived from the side-group elements of the periodic table of elements. Preferred salts of a metal and organo-metalic compounds useful in compositions in accordance with the invention include Cu, Ag, Ce, Fe, Cr, Co, Ni, V, Mn. Most preferred metal containing material are copper thiourea complex, copper acetyl, acetonate, copper saccarinate, copper naphenoate, nickel acetyl acetonate, nickel salicylate, vanadium saccarinate, iron chloride, chromium salicylate, chromium acetate.

Preferred dental/medical compositions in accordance with the invention comprise at least a monomer having at least one polymerizable group, a polymerizable monomer as diluent, a filler and a stabilizer.

The monomer preferably has at least one polymerizable group is a mono- or polyfunctional (meth) acrylate or a macromonomer. Preferably monomers are 2,2-Bis-[p-(2-hydroxy-3-methacryloyloxypropoxy)-phenyl]-propane, 7,7,9-trimethyl-4,13-dioxo-3,14-dioxa-5,12-diazahexadecan-1,16-diol methacrylate, dipentaerthrytrolpentamethacrylate monophosphate, α,ω-methacryloyl terminated epoxide-amine macromonomers, α,ω-methacryloyl terminated epoxide-carboxylic acid macromonomers, α,ω-methacryloyl terminated epoxide-phenol macromonomers.

Usable polymerizable diluents are mono(meth) acrylates and polyfunctional (meth) acrylates, such as polyalkylenoxide di-(meth) acrylates or poly(meth) acrylates, urethane di(meth) acrylates or poly (meth) acrylates, vinyl-, vinylenor vinyliden-, acrylate- or methacrylate substituted spiroorthoesters, spiroorthocarbonates or bicycloorthoesters. Preferably were used diethyleneglycol dimethacrylate, triethyleneglycol dimethacrylate, 3,(4),8,(9)-dimethacryloyloxymethyltricyclodecane, dioxolan bismeth-acrylate, glycerol trimethacrylate, furfuryl methacrylate in an amount of 5 to 80 weight percent.

The filler may be inorganic fillers such as $La_2O_3$, $ZrO_2$, $BiPO_4$, $CaWO_4$, $BaWO_4$, $SrF_2$, $Bi_2O_3$, glasses or an organic fillers, such as polymer granulate or a combination of organic/or inorganic fillers.

A preferred cement composition in accordance with the invention has from 10 to 30 weight percent of an acidic monomer having at least one polymerizable group, 15 to 35 weight percent of a polymerizable monomer as diluent and a stabilizer, 50 to 65 weight percent of a filler and 0.34 to 12 weight percent of the polymerization initiator.

A preferred composite composition in accordance with the invention has from 5 to 25 weight percent of an acidic monomer having at least one polymerizable group, 5 to 20 weight percent of a polymerizable monomer as diluent and a stabilizer, 50 to 85 weight percent of a filler and 0.34 to 12 weight percent of the polymerization initiator.

A preferred sealer composition in accordance with the invention has from 15 to 55 weight percent of an acidic monomer having at least one polymerizable group, 20 to 40 weight percent of a polymerizable monomer as diluent and a stabilizer, 10 to 50 weight percent of a filler and 0.34 to 12 weight percent of the polymerization initiator.

In order to obtain a dental/medical composition with a sufficient shelf-life it is necessary to distribute all parts of the initiator system in such a manner that they do not react by themselves and that they will not be decomposed by other substances.

Preferably the initiator system is distributed between a liquid component and a powder component wherein the liquid component includes acidic monomer having at least one polymerizable group, polymerizable monomer as diluent, peroxide and stabilizer; and the powder component includes filler, modified ascorbic acid, metal salt and an organic metal compound and amine. Also, it is preferred that the initiator system be distributed between a liquid component and a powder component, wherein the liquid component includes acidic monomer having at least one polymerizable group, polymerizable monomer as diluent, peroxide, amine and stabilizer, and the powder component includes filler, modified ascorbic acid and metal salt or an organic metal compound.

Surprisingly, peroxide and tertiary amine do not react while stored at 23° C. for over 18 months or while stored at 43° C. for over 18 months.

The invention will now be described with reference to examples and comparative examples.

COMPARATIVE EXAMPLE 1

Powder:
69.818 g of silylated Strontium-alumo-silicate glass, 0.280 g of ascorbic acid and 0.042 g of copper thio urea complex were mixed to form a uniformly dispersed powder mixture.

Liquid:

29.670 g of an ammonium salt of dipentaerthrytrolpentamethacrylate monophosphate and 2-(dimethyl)aminoethyl methacrylate (AP-1) containing 19.780 g of triethylenglycol dimethacrylate, 0.500 g of tert-butyl peroxy benzoate, 0.025 g of N,N-bis(hydroxyethyl)-p-toluidine and 0.050 g of 2,6-di-tert.-butyl-p-cresol were mixed to form a homogeneous liquid.

Immediately before use powder and liquid were mixed in the weight ratio of 1.60:1.00 to form a uniformly dispersed homogeneous mixture of powder and liquid. The the setting time is 3.81 minutes.

tetrahydrofuran. Removal of solvent in vacuo from the combined filtrate yielded 23.48 g (87.1%) of 3,5-Bis (trimethylsiloxy)-6-O-palmitoyl-L-ascorbic acid.

m.p. 72–74° C. IR(KBr, neat) 1252, 848, 759 (all Me$_3$Si) $^{13}$C-NMR(CDCL$_3$): 170.5 (s, 1); 118.7 (s, 2); 154.2 (s, 3); 74.4 (s, 4); 63.9 (s, 5); 68.8 (s, 6); 173.7 (s, 7); 34.1 (s, 8); 24.8 (s, 9), 29.6 (m, 10–19), 31.9 (s, 20); 22.6 (s, 21), 14.1 (s, 22); −0.1 (s, 23); 0.4 (s, 24) $^1$H-NMR(CDCL$_3$) δ:4.70 (d, 1 H, J=3 Hz, C4); 4.234–4.20 (qur, 1 H, C5); 4.12 (d, 2 H, J=1Hz, C6); 2.32–2.26 (t, 2 H, J=7.6 Hz, C8); 1.61–1.55 (qui, 2 H, C9); 1.22 (m, 26 H, C10–C21); 0.84 (t, 3 H, J=6.6 Hz, C22); 0.24 (s, 9 H,TMS-23); 0.12 (s, 9 H,TMS-24)

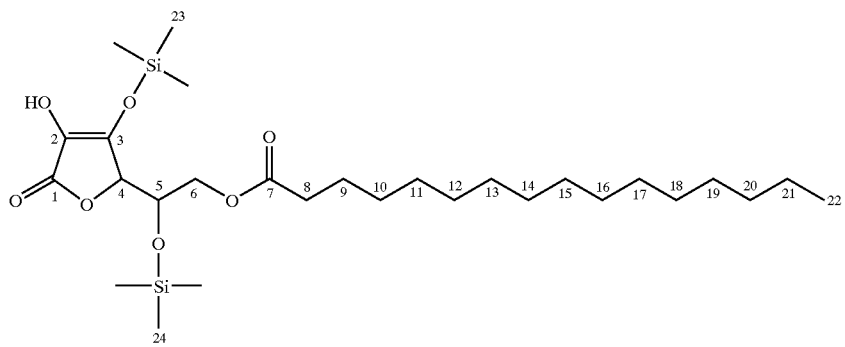

The samples were stored in open container at 30° C. and 70% relative humidity. Depending on the time of storage the following setting times of the same samples were estimated according ISO 9917 (Table 2, FIG. 1).

Setting times (ST) of Composite Compositions made in accordance with Comparative Example 1 are stored at 30° C. and 70% of relative humidity are shown in Table 2.

TABLE 2

| time days | ST min | dST min |
|---|---|---|
| 0 | 3.81 | 0.00 |
| 1 | 4.52 | 0.71 |
| 2 | 4.75 | 0.94 |
| 5 | 4.92 | 1.11 |
| 6 | 5.30 | 1.49 |
| 7 | 5.55 | 1.74 |
| 8 | 6.23 | 2.42 |
| 9 | 6.60 | 2.79 |
| 12 | >8.00 | 4.19 |

EXAMPLE 1

Synthesis of Silylated Ascorbic Acid

In a 500 ml 3-necked flask fitted with a reflux condenser, nitrogen inlet, droping funnel and magnetic stirring bar was placed 20.00 g (48.3 mmol) of 6-O-palmitoyl-L ascorbic acid in 130 ml of dry tetrahydrofuran and 0.26 g (4.8 mmol) of ammonium chloride. 12.85 g (79.6 mmol) of hexamethyldisilazane in 30 ml of dry tetrahydrofuran was then added under nitrogen and the mixture was stirred for 5 hours at 23° C. After additional stirring and heating for 2 hours at 50° C. the reaction was finished, as evidenced by the end of ammonia evolution. The reaction mixture was filtered and the ammonium chloride was rinsed with 2×20 ml of dry $^1$H-NMR spectra and HPLC leads to the conclusion that in average two of the three OH groups are silylated. HPLC and FAB mass spectroscopic investigations (M=487, 557, 631) prove, that a mixture of silylated ascorbic acid palmitate was obtained having one, two or three trimethylsilyl moieties.

Powder:

50.038 g of silylated Strontium-alumo-silicate glass, 0.100 g of silylated ascorbic acid and 0.038 g of copper thio urea complex were mixed homogeneously.

Liquid:

25.000 g of 2-(dimethyl) aminoethyl methacrylate (AP-1) containing 10.500 g of triethylenglycol dimethacrylate, 0.269 g of tert.-butyl peroxy (3,5,5-trimethylhexanoate), 0.036 g of N,N-bis(hydroxyethyl)-p-toluidine and 0.035 g of 2,6-di-tert.-butyl-p-cresol were mixed homogeneously.

Table 3 shows Setting times (ST) of a composite comprising initiator stored at 30° C. and 70% of relative humidity. Difference dST of initial setting time immediately measured after preparation and setting times after storage at 30° C. and 70% relative humidity

TABLE 3

| time days | ST min | dST min |
|---|---|---|
| 0 | 3.23 | 0.00 |
| 1 | 3.30 | 0.07 |
| 2 | 3.50 | 0.27 |
| 5 | 3.63 | 0.40 |
| 6 | 3.58 | 0.35 |
| 7 | 3.50 | 0.27 |
| 8 | 3.47 | 0.24 |
| 9 | 3.50 | 0.27 |
| 12 | 3.42 | 0.19 |

TABLE 3-continued

| time days | ST min | dST min |
|---|---|---|
| 28 | 3.67 | 0.44 |
| 33 | 3.75 | 0.52 |
| 42 | 4.05 | 0.82 |

FIG. 1 is a graph of differences in setting time (d ST) verses time for compositions made in Example 1 indicated along line 10 and compositions made in Comparative Example 1 indicated along line 20.

Immediately before use powder and liquid in the weight ratio 1.60:1.00 were homogeneously mixed. The compressive strength is 243±25 MPa and the E-modulus 2809±309 MPa. The working time was 3.23 minutes. After 3 weeks storing at 30° C. and 70% relative humidity the setting time was 4.05 (FIG. 1).

EXAMPLE 2

Synthesis of Ascorbic Acid—Acetal 3.055 g (7.375 mmol) of ascorbic acid palmitate, 0.783 g (7.375 mmol) of benzaldehyde and 0.001 g of p-toluen sulfonic acid were dissolved in 50 ml of toluene. Than the water was removed by azeotropic distillation. The crude product was filtered off and recrystallized.

$^{13}$C-NMR: 174.9 (1), 120.6 (2), 154.9 (3), 76.9 (4), 65.1 (5), 67.6 (6), 173.7 (7) ppm

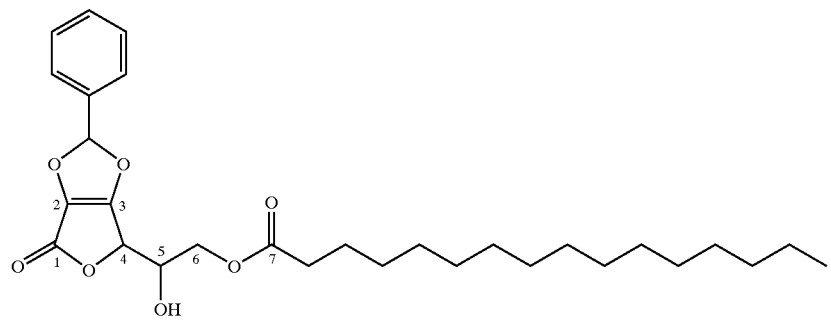

Powder:

37.212 g of silylated Strontium-alumo-silicate glass, 0.075 g of an acetal of ascorbic acid with benzaldehyde and 0.028 g of copper thiourea complex were mixed homogeneously.

Liquid:

15.840 g of 2-(dimethyl)aminoethyl methacrylate (AP-1) containing 10.560 g of triethylenglycol dimethacrylate, 0.200 g of tert.-butyl peroxy (3,5,5-trimethylhexanoate), 0.027 g of N,N-bis(hydroxyethyl)-p-toluidine and 0.027 g of 2,6-di-tert.-butyl-p-cresol were mixed homogeneously.

Immediately before use powder and liquid were mixed in the weight ratio of 1.60:1.00 homogeneously. The setting time is 3.25 minutes.

APPLICATION EXAMPLE 1 (DENTAL ADHESIVE)

Powder:

23.000 g of silylated Strontium-alumo-silicate glass, 0.875 g of silylated Strontium-alumo-silicate glass compris-ing 2 weight percent copper thio urea complex, 1.000 g of silylated Strontium-alumo-silicate glass containing 5 weight percent silylated ascorbic acid and 0.125 g aerosil A 200 were mixed homogeneously.

Liquid:

18.0000 g of 2-(dimethyl)aminoethyl methacrylate (AP-1) comprising 30 weight percent triethylene glycol dimethacrylate, 4.5000 g of macromonomer M-1 (syntheseized by reaction of two moles methacrylic acid, two mols 2,2-bis-[4-(2,3-epoxypropoxy)-phenyl]-propane and one mole adipic acid) comprising 30 weight percent triethylene glycol dimethacrylate, 10.6328 g of triethylene glycol dimethacrylate, 0.0167 g of N,N-bis(β-hydroxyethyl)-p-toluidine, 0.5049 g of tert. butyl peroxy benzoate, 0.0113 g of 2,6-di-tert.-butyl-p-cresol were mixed homogeneously.

Immediately before use powder and liquid are mixed homogeneously in the weight ratio of 1.60:1.00. The setting time is 3:48 minutes. The composite shows the following mechanical properties: compressive strength of 200±6 MPa, a flexural strength of 50.3±4.7 and an E-modules of 4392±283 MPa.

APPLICATION EXAMPLE 2 DENTAL FILLING MATERIAL

Powder:

25.1820 g of silylated Strontium-alumo-silicate glass, 1.0773 g of silylated Strontium-alumo-silicate glass comprising 2 weight percent copper thio urea complex and 0.5387 g of silylated Strontium-alumo-silicate glass containing 10 weight percent silylated ascorbic acid were homogeneously mixed.

Liquid:

18.0000 g of 2-(dimethyl)aminoethyl methacrylate (AP-1) comprising 30 weight percent triethylene glycol dimethacrylate, 4.5000 g of macromonomer M-1 (syntheseized by reaction of two mols methacrylic acid, two mols 2,2-bis-[(4-(2,3-epoxypropoxy)-phenyl]-propane and one mole adipic acid) comprising 30 weight percent triethylene glycol dimethacrylate, 10.6328 g of triethylene glycol dimethacrylate, 0.0167 g of N,N-bis(β-hydroxyethyl)-p-toluidine, 0.5049 g of tert. butyl peroxy benzoate, 0.0113 g of 2,6-di-tert.-butyl-p-cresol were mixed homogeneously.

Immediately before use powder and liquid are mixed in the weight ratio of 3.20:1.00 homogeneously. The working time is 3.75 minutes and the setting time is 3:00 minutes. The mixture is applied to a tooth in a patient's mouth and polymerizes to form polymeric composite filling material.

The composite has a compressive strength of 256.6±11.9 MPa, a flexural strength of 87.0±3.4 and E-modules of 7780±785 MPa.

It will be apparent to those skilled in the art that various modifications and changes may be made in the practice and use of the present invention without departing from the scope thereof as set forth in the following claims.

We claim:

1. A composition comprising:
   from 0.2 to 5 percent by weight of a peroxide,
   from 0.2 to 3 percent by weight of a metal containing material, and
   from 0.1 to 3 percent by weight of a protected reducing agent characterized by the following structure:

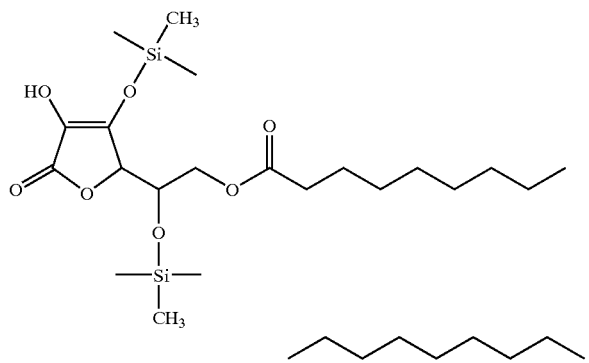

2. The composition of claim 1 wherein said peroxide is selected from the group consisting of a diacyl peroxide, a perester, a perketale, a peroxy dicarbonate, a dialkyl peroxide, a ketone peroxide, a alkyl hydroxyperoxide, 2,5-dimethyl-2,5-di(benzolyperoxy)hexane, tert.-butylamyl peroxide, di-(tert.-butyl) peroxide, cumen hydo peroxide, tert.-butylhydro peroxide, tert.-butyl-peroxy-(3,5,5-trimethyl hexanoate), tert.-butylperoxy benzoate and tert.-butylperoxy-2-ethyihexyl carbonate.

3. The composition of claim 1, wherein the composition further comprises an amine.

4. The composition of claim 1 wherein said peroxide decomposes by at most fifty percent by weight of said peroxide within 10 hours at a temperature of at least 75° C.

5. The composition of claim 3 wherein said amine comprises up to 1 percent by weight of said composition and said amine is an alkyl aryl amine, a dialkyl aryl amine or a trialkyl amine.

6. The composition of claim 3 wherein said amine comprises from 0.001 to 0.5 percent by weight of said composition.

7. The composition of claim 3 wherein said amine comprises from 0.01 to 0.2 percent by weight of said composition.

8. The composition of claim 1 wherein said metal containing material is a salt of a metal or an organo-metalic compound.

9. The composition of claim 1 wherein said metal of said metal containing material is selected from the group consisting of copper, silver, cerium, iron, chromium, nickel, vanadium and manganese.

10. The composition of claim 1 wherein said metal containing material is a acetate, salicylate, naphenoate, thiourea complex, acetylacetonate or ethylene tetramine acidic acid.

11. The composition of claim 1 further comprising from 10 to 30 weight percent of an acidic monomer, 15 to 35 weight percent of a polymerizable monomer, and 50 to 65 weight percent of filler.

12. The composition of claim 1 further comprising from 5 to 25 weight percent of an acidic monomer, 5 to 20 weight percent of a polymerizable monomer and 50 to 85 weight percent of filler.

13. The composition of claim 1 further comprising 15 to 55 weight percent of an acidic monomer, 20 to 40 weight percent of a polymerizable monomer, and 10 to 50 weight percent of filler.

* * * * *